United States Patent [19]
Dyke et al.

[11] Patent Number: 5,925,636
[45] Date of Patent: Jul. 20, 1999

[54] BENZOFURAN CARBOXAMIDES AND THEIR THERAPEUTIC USE

[75] Inventors: Hazel Joan Dyke; Christopher Lowe; John Gary Montana, all of Cambridge, United Kingdom

[73] Assignee: Darwin Discovery Limited, United Kingdom

[21] Appl. No.: 08/859,509

[22] Filed: May 20, 1997

[30] Foreign Application Priority Data

May 20, 1996 [GB] United Kingdom .................. 9610515
Dec. 5, 1996 [WO] WIPO ...................... PCT/GB96/03012
Apr. 22, 1997 [GB] United Kingdom .................. 9708070

[51] Int. Cl.$^6$ ...................... C07D 307/83; C07D 401/12; A61K 31/34
[52] U.S. Cl. .......................... 514/242; 514/256; 514/337; 514/422; 514/469; 544/212; 544/328; 544/329; 546/284.1; 548/525; 549/462; 549/468; 549/471
[58] Field of Search ................................... 544/212, 328, 544/329; 546/284.1; 548/525; 549/462, 468, 471, 242; 514/256, 337, 422, 469

[56] References Cited

FOREIGN PATENT DOCUMENTS

| | | |
|---|---|---|
| 0187387 | 7/1986 | European Pat. Off. . |
| 0637586 | 2/1995 | European Pat. Off. . |
| 637 586 | 2/1995 | European Pat. Off. . |
| 0685475 | 12/1995 | European Pat. Off. . |
| 0771794 | 5/1997 | European Pat. Off. . |
| 9203427 | 3/1992 | WIPO . |
| 9408962 | 4/1994 | WIPO . |
| 9603399 | 7/1995 | WIPO . |
| 9636595 | 11/1996 | WIPO . |
| 9636596 | 11/1996 | WIPO . |
| 9636611 | 11/1996 | WIPO . |

OTHER PUBLICATIONS

Damasio, Alzheimer's Disease and related dementias, Cecil Textbook of Medicine, 20th Edition, vol. 2, pp. 1992–1996, 1996.
Christensen et al., Chem. Abstract 76:99520, 1972.

*Primary Examiner*—Mukund J. Shah
*Assistant Examiner*—Deepak R. Rao
*Attorney, Agent, or Firm*—Saliwanchik, Lloyd & Saliwanchik

[57] ABSTRACT

Compounds having the formula (i),

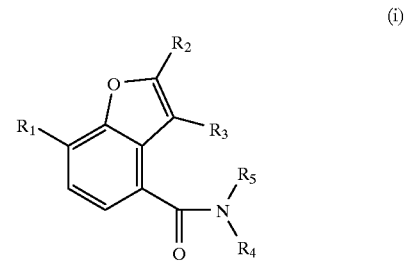

wherein the groups $R_1$, $R_2$, $R_3$, $R_4$ and $R_5$ are defined herein. The compounds of the present invention can be utilized to treat disease states capable of being modulated by inhibition of proteins which mediate cellular activity, such as tumor necrosis factor (TNF) and/or phosphodiesterase IV (PDE IV).

29 Claims, No Drawings

BENZOFURAN CARBOXAMIDES AND THEIR THERAPEUTIC USE

FIELD OF THE INVENTION

The present invention relates to novel benzofuran carboxamides, and to their formulation and use as pharmaceuticals.

BACKGROUND OF THE INVENTION

EP-A-0637586 discloses benzofuran derivatives, including 4-carboxamides, ad acetylcholine esterase inhibitors.

WO-A-9408962 discloses benzofuran analogues as fibrinogen receptor antagonists.

WO-A-9203427 discloses benzofuran-2-carboxamides, with a 3-substituent selected from hydroxy, acyloxy, alkoxy, optionally alkyl-substituted aminoalkoxy, alkylsulphonylamino, optionally alkyl-substituted aminoalkylsulphonyl or arylsulphonylamino, as a remedy for osteoporosis.

EP-A-0685475 discloses benzofuran-2-carboxamides as anti-inflammatory agents.

WO-A-9603399 discloses dihydrobenzofuran-4-carboxamides as inhibitors of phosphodiesterases.

Phosphodiesterases (PDE) and Tumour Necrosis Factor (TNF), their modes of action and the therapeutic utilities of inhibitors thereof, are described in WO-A-9636595, WO-A-9636596 and WO-A-9636611, the contents of which are incorporated herein by reference. The same documents disclose benzofuran derivatives having utility as PDE and TNF inhibitors.

SUMMARY OF THE INVENTION

This invention is based on the discovery of novel compounds that can be used to treat disease states, for example disease states associated with proteins that mediate cellular activity, for example by inhibiting tumour necrosis factor and/or by inhibiting phosphodiesterase IV. According to the invention, the novel compounds are of formula (i):

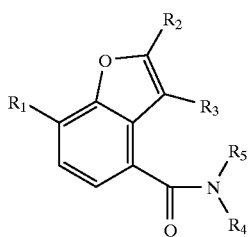

(i)

wherein
$R_1$ represents alkoxy optionally substituted with one or more halogens;

either $R_2$ and $R_3$, which may be the same or different, are each selected from the group consisting of H, CO-heteroaryl, CO-alkylaryl, alkyl-CO-alkyl, alkyl-CO-heteroaryl and alkyl-CO-alkylaryl, provided that $R_2$ and $R_3$ are not both H; and $R_5$ is selected from the group consisting of aryl, heteroaryl, heterocyclo, arylalkykl, heteroarylalkyl or heterocycloalkyl;

or $R_2$ and $R_3$ are the same or different and are each aryl selected from the group consisting of H, aryl, arylalkyl, heteroaryl, alkyl and CO-alkyl; and $R_5$ is aryl or heteroaryl (except 4-pyridyl) optionally substituted with one or more substituents $R_{13}$ or alkyl-$R_{13}$;

$R_4$ is selected from the group consisting of H, arylalkyl, heteroarylalkyl, heterocycloalkyl, $S(O)_m R_{10}$ or alkyl optionally substituted with one or more substituents chosen from hydroxy, alkoxy, $CO_2R_7$, $SO_2NR_{11}R_{12}$, $CONR_{11}R_{12}$, —CN, carbonyl oxygen, $NR_8R_9$, $COR_{10}$ and $S(O)_n R_{10}$;

in $R_4$ and/or $R_5$, the aryl/heteroaryl/heterocyclo portion may be optionally substituted with one or more substituents alkyl-$R_{13}$ or $R_{13}$;

$R_7$ is selected from the group consisting of H, alkyl, arylalkyl, heteroarylalkyl or heterocycloalkyl;

$R_8$ is selected from the group consisting of H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl;

$R_{10}$ is selected from the group consisting of alkyl, aryl, heteroaryl, heterocyclo, arylalkyl, heteroarylalkyl or heterocycloalkyl;

$R_9$, $R_{11}$ and $R_{12}$, which may be the same or different, are each selected from the group consisting of H and $R_{10}$;

$R_{13}$ is selected from the group consisting of alkyl optionally substituted by one or more halogen, alkoxy, aryl, heteroaryl, heterocyclo, hydroxy, aryloxy, heteroaryloxy, heterocyclooxy, arylalkyloxy, heteroarylalkyloxy, heterocycloalkyloxy, $CO_2R_3$, $CONR_{11}R_{12}$, $SO_2NR_{11}R_{12}$, halogen, —CN, —$NR_8R_9$, $COR_{10}$, $S(O)_n R_{10}$ and carbonyl oxygen (where appropriate);

m represents 1 or 2;

n represents 0–2;

or a pharmaceutically-acceptable salt thereof.

Combinations of substituents and/or variables are only permissible if such combinations result in stable compounds.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means alkyl-O— group in which the alkyl group is as previously described. Aryloxy means an aryl-O— group in which the aryl group is as defined below. Heteroaryloxy means a heteroaryl-O— group and heterocyclooxy means a heterocyclo-O— group in which the heteroaryl and heterocyclo group are as defined below. Arylalkyloxy means an aryl-alkyl-O— group. Heteroarylalkyloxy means a heteroaryl-alkyl-O— group and heterocycloalkyloxy means a heterocyclo-alkyl-O— group. Alkylamino means an alkyl-N— group in which the alkyl group is as previously defined, arylamino means aryl-N— and heteroarylamino means an heteroaryl-N— group (aryl and heteroaryl defined below). Thioalkyl means an alkyl-Sgroup. Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkylgroup wherein the aryl and alkyl are as described herein. Heteroarylalkyl means a heteroaryl-alkyl group and heterocycloalkyl means a heterocyclo-alkyl group. Alkylcarbonyl means an alkyl-CO— group in which the alkyl group is as previously described. Arylcarbonyl means an aryl-CO— group in which the aryl group is as previously described. Heteroarylcarbonyl means a heteroaryl-CO— group and heterocyclocarbonyl means a heterocyclo-CO— group. Arylsulphonyl means an aryl-$SO_2$— group in which the aryl group is as previously described. Heteroarylsulphonyl means a heteroaryl-$SO_2$— group and heterocyclosulphonyl means a heterocyclo-$SO_2$— group. Alkoxycarbonyl means an alkyloxy-CO— group in which the alkoxy group is as previously described. Alkylsulphonyl means an alkyl-$SO_2$— group in which the alkyl group is as previously described. Carbonyl oxygen means a —CO— group. It will be appreciated that a carbonyl oxygen can not be a substituent on an aryl or heteroaryl ring. Carbocyclic ring means about a 5 to about a 10 membered monocyclic or multicyclic ring system which may saturated or partially unsaturated. Heterocyclic ring means about a 5 to about a 10 membered monocyclic or multicyclic ring system (which may be saturated or partially unsaturated) wherein one or more of the atoms in the ring system is an element other than carbon chosen amongst nitrogen, oxygen or sulphur atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur, if desired, a N atom may be in the form of an N-oxide. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Halogen means fluorine, chlorine, bromine or iodine.

Compounds of the invention are useful for the treatment of TNF mediated disease states. "TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated with TNF. As TNF-β (also known as lymphotoxin) has close structural homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including: asthma, chronic bronchitis, chronic obstructive airways disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, sepsis, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. PDE IV inhibitors may also be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation of TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%.

The invention further provides a process for the preparation of a compound of formula (i), in which $R_1$ etc. m and n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction sequence. Suitable protecting groups for such functionality will be apparent to those skilled in the art. For specific details, see Protective Groups in Organic Synthesis, Wiley Interscience, T W Greene. Thus the process for preparing compounds of formula (i) in which $R_4$ contains an —OH comprises deprotecting (for example by hydrogenolysis or hydrolysis) a compound of formula (i) in which $R_4$ contains an appropriate —OP wherein P represents a suitable protecting group (e.g. benzyl or acetyl).

It will be appreciated that where a particular stereoisomer of formula (i) is required, this may be obtained by conventional solution techniques such as high performance liquid chromatography or the synthetic processes herein described may be performed using the appropriate homochiral starting material.

A process for the preparation of a compound of formula (i) comprises reaction of an appropriate carboxylic acid of formula (ii) with a suitable amine of formula (iii)

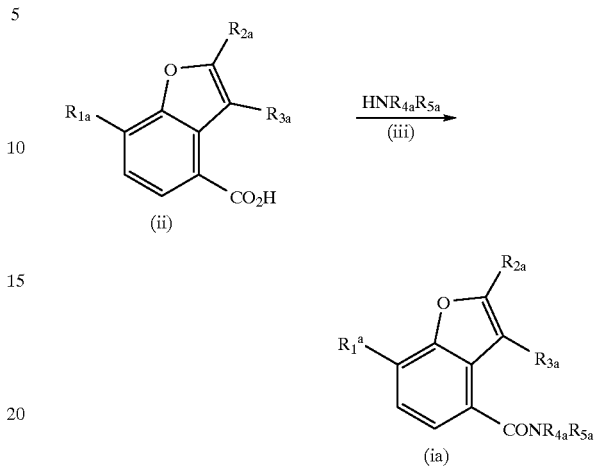

wherein $R_{1a}$ represents $R_1$ as defined in relation to formula (i) or a group convertible to $R_1$ and $R_{2a}$–$R_{5a}$ similarly represent $R_2R_5$ or groups convertible to $R_2R_5$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$; and thereafter, if required converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$. The reaction of a carboxylic acid of formula (ii) with an amine of formula (iii) may be carried out under any suitable conditions known to those skilled in the art. Preferably, the reaction is carried out in the presence of a suitable base, for example an amine such as triethylamine, preferably in an appropriate solvent such as dichloromethane. In some cases a stronger base, such as sodium hydride, and a polar solvent such as dimethylformamide, will be required. Preferably, the carboxylic acid is converted into an acid chloride, mixed anhydride or other activated intermediate prior to reaction with an amine of formula (iii).

Carboxylic acids of formula (ii) and amines of formula (iii) are either commercially available, previously described compounds or are prepared using standard procedures known to those skilled in the art. For example, a carboxylic acid of formula (ii) is conveniently prepared from an appropriate benzofuran of formula (v), using standard procedures known to those skilled in the art. For example, a benzofuran of formula (v) can be formulated to provide an aldehyde of formula (iv), which can then by oxidised to provide the corresponding acid of formula (ii). Alternatively, a benzofuran of formula (v) can be brominated to provide a bromide of formula (vi), which can then be converted into a carboxylic acid of formula (ii), for example by organometal-catalysed carboxylation, for example by a palladium-catalysed reaction.

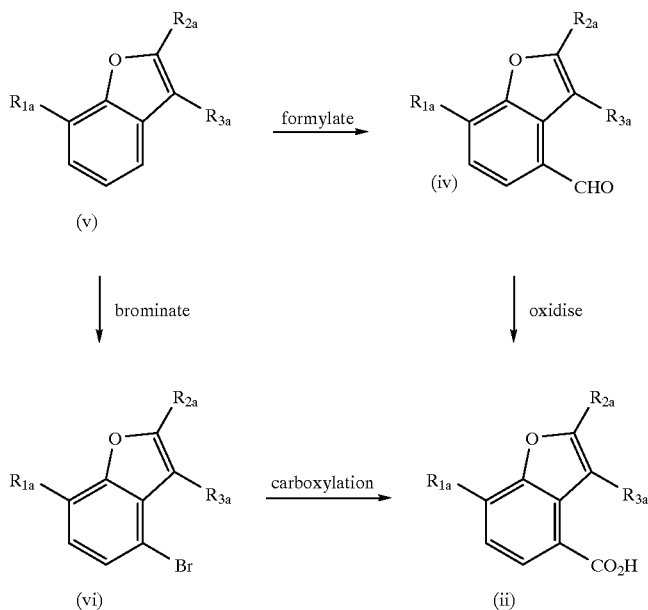

A compound of formula (ia) may also be prepared by reaction of a carboxylic acid of formula (ii) with an amine (iii) to provide a compound of formula (ia) in which $R_{4a}$ is H, followed by reaction with an agent $R_{4a}Y$ (vii) in which Y is a suitable leaving group such as a halogen. The first reaction can be carried out as described above. Preferably, the carboxylic acid is converted into an acid chloride, mixed anhydride or other activated intermediate prior to reaction with the amine (iii). The reaction with agent (vii) may be carried out under any suitable conditions known to those skilled in the art. It may be carried out in the presence of a suitable base, e.g. sodium hydride, preferably in an appropriate solvent such as dimethylformamide. Agents (vii) are known or commercially available, or are prepared using standard procedures known to those skilled in the art. Such compounds include alkylating agents such as propyl bromide, acylating agents such as benzoyl chloride and sulphonylating agents such as methanesulphonyl chloride.

Compounds of formula (i) may also be prepared by interconversion of other compounds of formula (i). For example, a compound in which $R_4$ contains an alkoxy group may be prepared by appropriate alkylation of a compound in which $R_4$ contains a hydroxy group.

By way of further example, compounds in which $R_2$ and/or $R_3$ is alkyl may be prepared by reduction of compounds in which $R_2$ and/or $R_3$ is CO-alkyl using standard conditions known to those skilled in the art (for example hydrazine hydrate in the presence of a suitable base in an appropriate solvent). Other transformations may be carried out on compounds of formula (i) in which $R_2$ and/or $R_3$ contains a carbonyl group. Such transformations include, but are not limited to, alkylation. Compounds in which $R_2$ or $R_3$ contain an $COR_{10}$ group may be prepared from compounds in which $R_2$ or $R_3$ contain a CN group by addition of a suitable organometallic agent (such as Grignard reagent). Any of the above transformations may be carried out either at the end of the synthesis or on an appropriate intermediate.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injections or infusion techniques. In addition to the treatment of warm-blooded animals such as mice, rates, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tableting lubricants, for example magnesium stearate, disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixers, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions in the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emolients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remingtons's Pharmaceutical Sciences, and the British and US Pharmacopoeias.

Suitably, the compound of formula (i), or if appropriate a pharmaceutically-acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

Intermediate 1

2-Acetyl-7-methoxybenzofuran-4-carbonyl chloride

2-Acetyl-7-methoxybenzofuran-4-carboxylic acid (0.12 g) was suspended in anhydrous dichloromethane (4 ml) at room temperature under nitrogen and oxalyl chloride (0.1 ml) added followed by 3 drops of N,N-dimethylformamide. Evaporation in vacuo after 2 h afforded the title compound as a yellow solid (~0.5 g). TLC $R_f$ 0.60 (50% ethyl acetate in hexane)

Intermediate 2

2-Acetyl-7-methoxybenzofuran-4-carboxylic acid

A mixture of 2-acetyl-4-bromo-7-methoxybenzofuran (5 g), triphenylphosphine (98 mg), bis(triphenylphosphine) palladium (II) chloride (261 mg), triethylamine (2.85 ml) and water (1 ml) in tetrahydrofuran (25 ml) was purged with carbon monoxide gas in a Parr pressure reactor at 110 psi. This was heated to 110° C. (pressure now 220 psi) and left for a week. On cooling and release of pressure the mixture was dissolved in 50% dichloromethane-water (200 ml) and taken to pH 12 using aqueous sodium hydroxide (1M). The separated aqueous phase was acidified to pH1 using dilute hydrochloric acid (1M) and the resultant slurry extracted with dichloromethane (3×100 ml) then ethyl acetate (100 ml). These combined organic extracts were dried over magnesium sulphate, filtered and evaporated in vacuo to afford a yellow solid (2.58 g). TLC $R_f$ 0.61 (ethyl acetate)

Intermediate 3

2-Acetyl-4-bromo-7-methoxybenzofuran

A solution of bromine (5.5 ml) in methanol (100 ml) was added dropwise to a suspension of 2-acetyl-7- methoxybenzofuran (20 g) in methanol (300 ml) at 0° C. The ice bath was removed immediately and the mixture allowed to warm to room temperature. After 1 h conversion was incomplete, so further bromine (0.75 ml) in methanol (25 ml) was added and the mixture stirred overnight. The reaction was quenched using aqueous sodium metabisulphite solution (300 ml) producing a precipitate that was filtered off and dried in vacuo to afford a brown solid (17.4 g). TLC $R_f$ 0.90 (ethyl acetate)

Intermediate 4

2-Ethyl-7-methoxybenzofuran-4-carboxylic acid

2-Methyl-2-butene (9 g) was added to a solution of 2-ethyl-7-methoxybenzofurancarboxaldehyde (5 g) in 2-methyl-2-propanol (125 ml). A solution of sodium dihydrogen phosphate monohydrate (20.7 g) in water (15 ml) was added, followed by sodium chlorite (11.05 g). The resultant heterogeneous mixture was stirred vigorously for 30 minutes and then diluted with water (125 ml). The mixture was adjusted to pH 4 by the addition of 2M hydrochloric acid. The mixture was extracted with ethyl acetate (3×200 ml) and the combined organic extracts were washed with water (2×200 ml). The organic solution was concentrated to about 100 ml and then cooled to 10° C. The resultant precipitate was collected by filtration and dried at 50° C. in vacuo to afford a beige solid (4 g). mp 215–216° C.

Intermediate 5

2-Ethyl-7-methoxy-4-N-(3-carboethoxyphenyl)benzofuran carboxamide

2-Ethyl-7-methoxybenzofuran-4-carbonyl chloride (1.0 g) was added to a solution of ethyl 3-aminobenzoate (0.72 g) in dichloromethane (30 ml) at room temperature under an inert atmosphere and the reaction mixture stirred at room temperature overnight. The mixture was poured into dilute aqueous hydrochloric acid and extracted with ethyl acetate (2×50 ml). The combined organic extracts were washed with water (50 ml), brine (50 ml), dried (magnesium sulphate) and evaporated in vacuo to yield the title compound (1.39 g) as a white solid. mp 159–161° C.

The following compound was prepared according to the above procedure.

Intermediate 6

2-Ethyl-7-methoxy-4-N-(4-carboethoxyphenyl)benzofuran carboxamide

Prepared from 2-ethyl-7-methoxybenzufuran-4-carbonyl chloride (1.3 g) and ethyl 4-aminobenzoate (1.0 g) to yield the title compound (0.76 g) as a white solid. TLC $R_f$ 0.18 (25% ethyl acetate in hexane)

Intermediate 7 2-Ethyl-7-methoxybenzorufan-4-carbonyl chloride

2-Ethyl-7-methoxybenzofuran-4-carboxylic acid (4.05 g) was heated in dry toluene (100 ml) with thionyl chloride (14 ml) under nitrogen at 90° C. for 2 h. The solution was evaporated to dryness in vacuo and azeotroped with dry toluene (2×50 ml) to afford the title compound (4.4 g) as an off-white solid. mp 100–120° C.

Intermediate 8

7-Methoxy-2-[(pyridin-4-yl)carbonyl]benzofuran-4-carbonyl chloride hydrochloride The title compound was prepared in a similar manner to Intermediate 1.

Intermediate 9

7-Methoxy-2-[(pyridin-4-yl)carbonyl]benzofuran-4-carboxylic acid

2-[(Pyridin-4-yl)carbonyl]-4-bromo-7-methoxybenzofuran (3.3 g), triphenylphosphine (1 g), bis(triphenylphosphine)palladium (II) chloride (0.47 g), tri-ethylamine (14 ml), tetrahydrofuran (150 ml) and $H_2O$ (57 ml) were combined in a Parr pressure reactor. The vessel was purged with carbon monoxide, charge to 180 psi with carbon monoxide and then heated to 80° C. with stirring for 3 days. On cooling and release of pressure the tetrahydrofuran was removed in vacuo. The remaining aqueous mixture was basified to pH14 with 1N sodium hydroxide solution (250 ml) and washed with ethyl acetate (200 ml). The aqueous layer was then acidified to pH5 with acidic acid under ice bath cooling. The resulting precipitate was collected by filtration and dried to give a beige solid (2.97 g). M.S. M+H observed The following Intermediate was prepared by a similar procedure.

Intermediate 10

7-Methoxy-2-(2-thiazolocarbonyl)benzofuran-4-carboxylic acid

The title compound was obtained as a cream solid (625 mg). M.S. [M+H] observed.

Intermediate 11

4-Bromo-7-methoxy-2-[(pyridin-4-yl)carbonyl]benzofuran

Bromine (0.02 ml) was added to a mixture of 2-[(pyridin-4-yl)carbonyl]-7-methoxy benzofuran (0.1 g) in methanol (7 ml) cooled to −78° C. under a nitrogen atmosphere. The reaction mixture was allowed to warm to room temperature over 2.5 h. The reaction was then diluted with ethyl acetate (40 ml), washed with 5% sodium metabisulfite solution (2×20 ml), saturated sodium bicarbonate solution (40 ml), dried over magnesium sulphate and concentrated to dryness in vacuo to afford a pale yellow solid (0.05 g) as a 2:1 mixture of product:starting material by $^1$H nmr. TLC $R_f$ 0.65 (10% methanol in ethyl acetate)

Intermediate 12

4-Bromo-7-methoxy-2-(2-thiazolocarbonyl)benzofuran

A stirred solution of 7-methoxy-2-(2-thiazolcarbonyl)benzofuran (3.09 g) in methanol (160 ml) was cooled to 0° C. under an inert atmosphere and bromine (0.61 ml) added dropwise. Stirring was continued for 18 h at room temperature and the solvent was then removed in vacuo. The residue was partitioned between 5N potassium hydroxide (60 ml)/5% sodium metabisulfite (200 ml) and ethyl acetate (100 ml). The aqueous phase was extracted with ethyl acetate (3×60 ml), dried (magnesium sulphate) and concentrated in vacuo to give the title compound as a beige solid (2.83 g). TLC $R_f$ 0.55 (50% ethyl acetate in hexane)

Intermediate 13

7-Methoxy-2-[(Pyridin-4-yl)carbonyl]benzofuran

Sodium hydroxide (1.22 g) was added to a solution of o-vanillin (2.11 g) in ethanol (50 ml) at 55° C. under a nitrogen atmosphere. The reaction mixture was stirred for 10 minutes to give a yellow suspension. 4-(Bromoacetyl)pyridine hydrobomide (5 g) was then added portionwise and the solution heated at 55° C. for 12 h, then at 65–70° C. for a further 12 h. The reaction mixture was cooled to room temperature and the solvent removed in vacuo. The residue was partitioned between water (250 ml, containing sodium hydroxide (0.5 g)) and dichloromethane (2×200 ml). The combined organic phases were washed with water (100 ml), dried over magnesium sulphate, filtered and evaporated in vacuo onto silica gel. The compound was washed through a pad of silica with ethyl acetate, the ethyl acetate was removed in vacuo and the residue azeotroped with hexane. The resulting solid was washed with hexane and filtered to furnish the title compound (0.95 g) as a yellow solid. TLC $R_f$ 0.53 (ethyl acetate)

Intermediate 14

7-Methoxy-2-(2-thiazolocarbonyl)benzofuran

To a stirred solution of o-vanillin (2.95 g) in ethanol (70 ml) at 55° C. was added sodium hydroxide (1.7 g) and stirring continued for 10 minutes. 2-Bromoacetylthiazole hydrobromide (5.57 g) was then added portionwise and heating was continued for 5 h. The solution was allowed to cool and concentrated in vacuo. The residue was partitioned between water (200 ml) and ethyl acetate (100 ml) and extracted with ethyl acetate (3×70 ml), the combined organic phases were dried over magnesium sulphate and concentrated in vacuo to give a brown solid. Purification by flash chromatography on silica eluting with 50% ethyl acetate in hexane gave the title compound as orange needles (3.09 g). TLC $R_f$ 0.55 (50% ethyl acetate in hexane)

Intermediate 15

4-(Bromoacetyl)pyridine hydrobromide

4-Acetylpyridine (10 g) was combined with 48% hydrogen bromide solution (18 ml) and heated to 70° C. Bromine (4.7 ml) dissolved in 48% hydrogen bromine solution (5 ml) was then added dropwise and heating then continued for 2.5 h. The precipitate which formed was collected by filtration, washed with 1:1 methanol:hexane (20 ml) and dried in vacuo to give a cream solid (19.5 g) as 2:1 mixture of product:starting material by $^1$H nmr. mp 170–172° C.

The following Intermediate was prepared in a similar manner.

Intermediate 16

2-Bromoacetylthiazole hydrobromide

The title compound was obtained as a pale yellow solid (5.57 g). $^1$H NMR (d$_6$-DMSO) δ5.00 (2 H, CH$_2$), 8.2 (1 H, aromatic), 8.4 (1 H, aromatic).

Intermediate 17

2-Ethyl-7-methoxy-4-[N-(2-chloro-5-methoxycarbonyl)phenyl]benzofuran carboxamide 5-Carboxymethyl-2-chloroaniline (0.566 g) was treated with 2-ethyl-7-methoxybenzofuran-4-carbonyl chloride (0.50 g) as in Method A. Purification by flash chromatography on silica eluting with 50% ethyl acetate in hexane afforded a white solid (0.497 g) TLC $R_f$ 0.5 (50% ethyl acetate in hexane) mp 174–176° C.

Intermediate 18

2-Ethyl-7-methoxy-4-[N-(2,6-Dichloro-4-ethoxycarbonyl)phenyl]benzofuran carboxamide Ethyl 4-amino-3,5-dichlorobenzoate (0.815 g) was treated with 2-ethyl-7-methoxybenzofuran-4-carbonyl chloride (0.754 g) as in Method A. Purification by triturating the crude product with dichloromethane afforded a white solid (338 mg). TLC $R_f$ 0.15 (20% ethyl acetate in hexane) mp 165–166° C.

Intermediate 19

4-Nitrophenyl 7-methoxy-2-(2-thiazolocarbonyl)-benzofuran-4-carboxylate

To a stirred solution of 7-methoxy-2-(2-thiazolocarbonyl) benzofuran-4-carboxylic acid (625 mg) in dichloromethane (40 ml) were added 1-(3-dimethylaminopropyl)-3-ethylcarbodiimide hydrochloride (593 mg), 4-nitrophenol (430 mg) and 4-dimethylaminopyridine (catalytic amount). Stirring was continued for 20 h, then the precipitate was filtered off, washed with dichloromethane and dried in vacuo to give the title compound as a white solid (720 mg). $^1$H NMR (CDCl$_3$) δ4.2 (3 H, OCH$_3$), 7.1 (1 H, aromatic), 7.6 (2 H, aromatic), 7.8 (1 H, aromatic), 8.2 (1 H, aromatic), 8.3 (1 H, aromatic), 9.2 (1 H, aromatic)

The following Intermediate was prepared by a similar procedure.

Intermediate 20

4-Nitrophenyl 2-ethyl-7-methoxybenzofuran-4-carboxylate

The title compound (1.26 g) was obtained as a white solid. TLC $R_f$ 0.3 (50% ethyl acetate in hexane)

Example 1

2-Ethyl-7-methoxy-4-[N-(2-chloropyrid-3-yl)]benzofuran carboxamide (Method A)

Sodium hydride (0.3 g) was added to a solution of 3-amino-2-chloropyridine (0.88 g) in anhydrous N,N-dimethylformamide (10 ml) at room temperature under nitrogen. This stirred mixture was stirred at room temperature for 1.5 h before addition of 2-ethyl-7-methoxybenzofuran-4-carbonyl chloride (1.8 g) washed in with anhydrous N,N-dimethylformamide (5 ml). The brown mixture was heated at 60° C. for 4 h, allowed to cool, poured into water (100 ml) and extracted into ethyl acetate (2×50 ml). These organic extracts were washed with water (50 ml) and saturated brine (50 ml) then dried over magnesium sulphate, filtered and evaporated in vacuo to give a crude residue. Purification by column chromatography on silica eluting with hot ethyl acetate afforded a beige solid (0.53 g) after trituration with diethyl ether). TLC $R_f$ 0.35 (50% ethyl acetate in hexane) mp 124–125° C.

Example 2

2-Acetyl-7-methoxy-4-[N-(3bromo-5-methylpyrid-2-yl)] benzofuran carboxamide (Method B)

2-Amino-3-bromo-5-methylpyridine (0.64 g) in dry tetrahydrofuran (20 ml) was treated with sodium hydride (0.15 g; 60% dispersion in oil) under an inert atmosphere at ambient temperature of 15 minutes. A solution of 2-acetyl-7-methoxybenzofuran-4-carbonyl chloride (0.86 g) in dry tetrahydrofuran (10 ml) was added and then stirred overnight before evaporation in vacuo. Aqueous sodium bicarbonate (50 ml) was added and the mixture extracted with ethyl acetate (2×50 ml). These extracts were dried over magnesium sulphate, filtered and evaporated in vacuo. The crude residue was purified by column chromatography on silica eluting with 50% ethyl acetate in hexane to afford a pale yellow powder (95 mg). TLC $R_f$ 0.5 (50% ethyl acetate in hexane)

Example 3

2-Acetyl-7-methoxy-4-[N-(2-chlorophenyl)]benzofuran carboxamide (Method C)

A solution of 2-acetyl-7-methoxybenzofuran-4-carbonyl chloride (1 g) in anhydrous dichloromethane (100 ml) under nitrogen at 0° C., was treated with 2-chloroaniline (0.42 ml), triethylamine (1.2 g) and 4-dimethylaminopyridine (20 mg). This solution was allowed to warm to room temperature and stirred overnight. The reaction mixture was washed with saturated aqueous sodium bicarbonate (100 ml), water (100 ml) and saturated brine (100 ml) then dried over magnesium sulphate, filtered and evaporated in vacuo to give a crude residue. Purification by column chromatography on silica eluting with 50% ethyl acetate in hexane afforded a solid (137 mg). mp 179–181° C.

Example 4

2-Acetyl-7-methoxy-4-[N-(2,6-dimethylphenyl)] benzofuran carboxamide 2,6-Dimethylaniline (0.49 ml) was treated with 2-acetyl-7-methoxybenzofuran-4-carbonyl chloride (1 g) as in method C. Purification by column chromatography on silica eluting with 50% ethyl acetate in hexane afforded a solid (255 mg). TLC $R_f$ 0.23 (50% ethyl acetate in hexane) mp 225–226° C.

Example 5
2-Acetyl-7-methoxy-4-[N-(4-methoxyphenyl)]benzofuran carboxamide

4-Methoxyaniline (567 mg) was treated with 2-acetyl-7-methoxybenzofuran-4-carbonyl chloride (1.19 g) as in method C. Purification by column chromatography on silica eluting with 50% ethyl acetate in heptane afforded a yellow solid (103 mg). TLC $R_f$ 0.26 (50% ethyl acetate in heptane)

Example 6
2-Acetyl-7-methoxy-4-[N-(3-methylphenyl)]benzofuran carboxamide m-Toluidine (0.42 ml) was treated with 2-acetyl-7-methoxybenzofuran-4-carbonyl chloride (1 g) as in method C. Purification by column chromatography on silica eluting with 50% ethyl acetate in hexane afforded a yellow solid (200 mg). TLC $R_f$ 0.5 (50% ethyl hexane acetate in hexane) mp 193–195° C.

Example 7
2-Acetyl-7-methoxy-4-[N-(3,5-dichloropyrid-2-yl)]benzofuran carboxamide 2-Amino-3,5-dichloropyridine (0.758 g) was treated with 2-acetyl-7-methoxybenzofuran-4-carbonyl chloride (1.17 g) as in method B using N,N-dimethylformamide as a cosolvent. Purification by column chromatography on silica eluting with 3% methanol in dichloromethane afforded a yellow solid (13 mg). TLC $R_f$ 0.5 (50% ethyl acetate in hexane)

Example 8
2-Acetyl-7-methoxy-4-[N-(2-methylphenyl)]benzofuran carboxamide

2-Methylaniline (0.21 ml) was treated with 2-acetyl-7-methoxybenzofuran-4-carbonyl chloride (0.5 g) as in method C. Purification by column chromatography on silica eluting with 50% ethyl acetate in hexane afforded a yellow solid (128 mg). TLC $R_f$ 0.24 (50% ethyl acetate in hexane) mp 174–175° C.

Example 9
2-Acetyl-7-methoxy-4-[N-(4-methoxy-2-methylphenyl)]benzofurancarboxamide 4-Methoxy-2-methylaniline (0.56 ml) was treated with 2-acetyl-7-methoxybenzofuran-4-carbonyl chloride (1.0 g) as in method C. Purification by column chromatography on silica eluting with 50% ethyl acetate in hexane afforded a yellow solid (235 mg). TLC $R_f$ 0.25 (50% ethyl acetate in hexane) mp 217–218° C.

Example 10
2-Acetyl-7-methoxy-4-[N-(pyrimidin-4-yl)]benzofuran carboxamide

4-Aminopyrimidine (0.376 g) was treated with 2-acetyl-7-methoxybenzofuran-4-carbonyl chloride (1 g) as in method C. Purification by column chromatography on silica eluting with a 0–10% methanol in ethyl acetate gradient afforded a yellow solid (0.14 g). TLC $R_f$ 0.49 (10% methanol in ethyl acetate) mp 212–214° C.

Example 11
2-Acetyl-7-methoxy-4-[N-(2-trifluoromethylphenyl)]benzofurancarboxamide 2-Aminobenzotrifluoride (0.5 ml) was treated with 2-acetyl-7-methoxybenzofuran-4-carbonyl chloride (1.0 g) as in method B. Purification by column chromatography on silica eluting with 50% ethyl acetate in hexane afforded a yellow solid (0.12 g). mp 164–166° C.

Example 12
2-Acetyl-7-methoxy-4-[N-(2-ethylphenyl)]benzofuran carboxamide

2-Ethylaniline (0.48 g) was treated with 2-acetyl-7-methoxybenzofuran-4-carbonyl chloride (1.0 g) as in method C. Purification by column chromatography on silica eluting with 25% ethyl acetate in hexane afforded an off-white solid (310 mg). TLC $R_f$ 0.13 (25% ethyl acetate in hexane) mp 174–175° C.

Example 12
2-Acetyl-7-methoxy-4-[N-(3-methylpyrid-2-yl)]benzofuran carboxamide

2-Amino-3-picoline (0.32 ml) was treated with 2-acetyl-7-methoxybenzofuran-4-carbonyl chloride (0.73 g) as in method C. Purification by column chromatography on silica eluting with 5% methanol in dichloromethane afforded a yellow solid (0.12 g). TLC $R_f$ 0.40 (5% methanol in dichloromethane)

Example 14
2-Acetyl-7-methoxy-4-[N-(2-methoxyphenyl)]benzofuran carboxamide o-Anisidine (0.49 g) was treated with 2-acetyl-7-methoxybenzofuran-4-carbonyl chloride (1 g) as in method C. Purification by column chromatography on silica eluting with 30% ethyl acetate in hexane afforded a yellow solid (160 mg).

Example 15
2-Acetyl-7-methoxy-4-[N-(2-chloropyrid-3-yl)]benzofuran carboxamide

3-Amino-2-chloropyridine (509 mg) was treated with 2-acetyl-7-methoxybenzofuran-4-carbonyl chloride (1.0 g) as in method B. Purification by column chromatography on silica eluting with 25% ethyl acetate in hexane afforded a yellow solid (205 mg).

Example 16
2-Acetyl-7-methoxy-4-[N-(2-chloro-6-methylphenyl)]benzofurancarboxamide 2-Chloro-6-methylaniline (0.56 g) was treated with 2-acetyl-7-methoxybenzofuran-4-carbonyl chloride (1 g) as in method C. Purification by recrystallisation from dichloromethane afforded a brown solid (160 mg). TLC $R_f$ 0.4 (5%methanol in dichloromethane)

Example 17
2-Ethyl-7-methoxy-4-[N-(3-carboxyphenyl)]benzofuran carboxamide

A solution of 2-ethyl-7-methoxy-4-[N-(3-carboethoxyphenyl)]benzofuran carboxamide (0.78 g) in THF (25 ml) was treated with a solution of lithium hydroxide monohydrate (0.18 g) in water (25 ml) and the reaction mixture stirred at room temperature overnight. The reaction mixture was concentrated in vacuo, diluted with water (100 ml) and acidified with dilute aqueous hydrochloric acid. The resulting white precipitate was collected, washed with water and dried in vacuo to afford the title compound (0.68 g) as a white solid. TLC $R_f$ 0.35 (5% methanol in dichloromethane) mp 265–267° C.

The following compounds were prepared according to the above procedure.

Example 18
2-Ethyl-7-methoxy-4-[N-(4-carboxyphenyl)]benzofuran carboxamide

Prepared from 2-ethyl-7-methoxy-4-[N-(4-carboethoxyphenyl)]benzofuran carboxamide (0.67 g) to afford the title compound (0.59 g) as a white solid. TLC $R_f$ 0.4 (5% methanol in dichloromethane) mp 279–280° C.

Example 19
2-Ethyl-7-methoxy-4-[N-(2-chloro-5-carboxy)phenyl]benzofurancarboxamide Prepared from 2-ethyl-7-methoxy-4-[N-(2-chloro-5-methoxycarbonyl)phenyl]benzofuran carboxamide (0.31 g) to afford the title compound (0.282 g) as a white solid. TLC $R_f$ 0.6 (ethyl acetate) mp 278–279° C.

Example 20
2-Ethyl-7-methoxy-4-[N-(2,6-dichloro-4-carboxy)phenyl]benzofurancarboxamide Prepared from 2-ethyl-7-methoxy-4-[N-(2,6-dichloro-4-ethoxycarbonyl)phenyl]benzofuran carboxamide (292 mg) to afford the title compound (230 mg) as a white solid. TLC $R_f$ 0.6 (6% methanol in dichloromethane) mp 274–275° C.

Example 21
2-Ethyl-7-methoxy-4-[N-(5-chloropyrimidin-4-yl)]benzofurancarboxamide Sodium bis(trimethylsilyl)amine (2.9 ml) (1M solution in tetrahydrofuran) was added to a suspension of 4-amino-5-chloropyrimidine (0.25 g) in dry N,N-dimethylformamide (1 ml) at room temperature under nitrogen. After stirring for 1 h, a solution of 2-ethyl-7-methoxybenzofuran-4-carbonyl chloride (0.46 g) in dry N,N-dimethylformamide (1 ml) was added and the resultant mixture was stirred for 48 h. The mixture was concentrated in vacuo to remove tetrahydrofuran and water was added. The resultant solution was extracted with dichloromethane (3×25 ml) and the combined organic extracts were washed with saturated sodium chloride solution (25 ml), dried (magnesium sulphate) and concentrated in vacuo. Water (7 ml) was added to the residue and the resultant solid was collected by filtration. Purification by recrystallisation afforded an off white solid (0.12 g) TLC $R_f$ 0.25 (3:2 Ethyl Acetate:Hexane) mp 161–163° C.

Example 22
2-Ethyl-7-methoxy-4-[N-(3-methylthiotriazin-5-yl)]benzofuran carboxamide 5-amino-3-methylthiotriazine (0.3 g) was treated with 2-ethyl-7-methoxybenzofuran-4-carbonyl chloride (0.50 g) as in Method A. Purification by flash chromatography on silica eluting with 50%ethyl acetate in hexane afforded a cream solid (0.1 g) TLC $R_f$ 0.47 (50% ethyl acetate in hexane) M.S. [M+H] observed Example 23
2-Ethyl-7-methoxy-4-[N-4-pyrido[3,2-b]pyridinyl)]benzofurancarboxamide 4-aminopyrido[3,2-b]pyridine (0.36 g) was treated with 2-ethyl-7-methoxybenzofuran-4-carbonyl chloride (0.59 g) as in Method A. Purification by flash chromatography on silica eluting with 10% methanol in ethyl acetate followed by trituration with hexane afforded a pale yellow solid (0.23 g) TLC $R_f$ 0.52 (10% methanol in ethyl acetate) mp 155–157° C.

Example 23
2-[(Pyridin-4-yl)carbonyl]-7-methoxy-4-[N-(3,5-dichloropyridin-4-yl]benzofuran carboxamide Sodium hydride (0.3 g) was added to a solution of 4-amino-3,5-dichloropyridine (0.56 g) in dimethylformamide (10 ml) under an atmosphere of nitrogen. The reaction mixture was heated to 55° C. for 1 h then 2-[(pyridin-4-yl)carbonyl]-7-methoxybenzofuran-4-carbonyl chloride was added in one portion. Heating at 55° C. was continued for 2 h then at room temperature for 12 h. The reaction mixture was concentrated to dryness in vacuo to give the crude product. Purification by flash chromatography on silica eluting with ethyl acetate and then 20% methanol in ethyl acetate afforded a cream solid (0.3 g). TLC $R_f$ 0.36 (ethyl acetate) mp 250–252° C.

Example 25
7-Methoxy-2-(2-thiazolocarbonyl)-4-[N-(5-chloropyrimidin-4-yl)]benzofurancarboxamide To a stirred solution of 4-amino-5-chloropyrimidine (220 mg) in dimethylformamide (20 ml) under nitrogen was added sodium hydride (60% dispersion in oil) (135 mg) and stirring was continued for 3 h. 4-Nitrophenyl 7-methoxy-2-(2-thiazolocarbonyl)-benzofuran-4-carboxylate (720 mg) was then added and stirring was continued for a further 18 h. The solvent was removed in vacuo and the resulting residue was triturated with ethyl acetate then purified by flash chromatography eluting with 2% ammonium hydroxide/20% methanol in ethyl acetate. Further trituration with methanol yielded the title compound as a cream solid (165 mg). M.S. [M+H] observed mp 262–264° C. (dec)

The following examples were prepared from 4-nitrophenyl 2-ethyl-7-methoxybenzofuran-4-carboxylate and the appropriate amine according to the above procedure.

Example 26
2-Ethyl-7-methoxy-4-[N-(2,5-difluoropyrimidin-4-yl)]benzofurancarboxamide Prepared from 4-amino-2,5-difluoropyrimidine (190 mg) to give the title compound (95 mg) as an off-white solid. TLC $R_f$ 0.6 (50% ethyl acetate in hexane) mp 175–176° C.

Example 27
2-Ethyl-7-methoxybenzofuran-4-[(N-(1,3,5-trimethylpyrazol-4-yl)]carboxamide Prepared from 4-amino-1,3,5-trimethylpyrazole (165 mg) to give the title compound (222 mg) as a white solid. TLC $R_f$ 0.27 (10% methanol in ethyl acetate) mp 182–184° C.

Example 28
2-Acetyl-7-methoxy-4-[N-(3,5-dichloropyrid-4yl)]benzofurancarboxamide Sodium hydride (0.03 g) was added to a solution of 4-amino-3,5-dichloropyridine (0.08 g) in anhydrous N,N-dimethylformamide (1 ml) at room temperature under nitrogen. This stirred mixture was warmed to 60° C. for 1 hour before addition of 2-acetyl-7-methoxybenzofuran-4-carbonyl chloride (generated from 2-acetyl-7-methoxybenzofuran-4-carboxylic acid, 0.12 g) washed in with anhydrous N,N-dimethylformamide (2 ml). The brown mixture was heated at 60° C. for 4 hours, allowed to cool, poured into water (100 ml) and extracted into ethyl acetate (2×50 ml). These organic extracts were washed with water (50 ml) and saturated brine (50 ml) then dried over magnesium sulphate, filtered and evaporated in vacuo to give a crude residue (0.17 g). Purification by column chromatography on silica eluting with a 20–80% ethyl acetate in hexane gradient afforded a white solid (0.04 g). TLC $R_f$ 0.20 (50% ethyl acetate in hexane) mp 252–254° C.

Example 29
2-Acetyl-7-methoxy-4-[N-(pyrid-4-yl)]benzofurancarboxamide

A solution of 2-acetyl-7-methoxybenzofuran-4-carbonyl chloride (164 mg) in anhydrous dichloromethane (10 ml) under nitrogen at 0° C., was treated with 4-aminopyridine (0.07 g), triethylamine (0.12 g) and 4-dimethylaminopyridine (2 mg). This solution was allowed to warm to room temperature and stirred overnight. The reaction mixture was washed with saturated aqueous sodium bicarbonate (10 ml), water (10 ml) and saturated brine (10 ml) then dried over magnesium sulphate, filtered and evaporated in vacuo to give a crude residue. Purification by column chromatography on silica eluting with 5% methanol in dichoromethane afforded a pale yellow solid (85 mg). TLC $R_f$ 0.27 (5% methanol in dichloromethane) mp 247–248° C. (dec)

Assay methods

The assays used to confirm the phosphodiesterase IV inhibitory activity of compounds of formula (i) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treated phosphodiesterase IV-related disease states in those assays.

The ability of compounds of formula (i) to inhibit TNF production in human peripheral blood mononuclear cells (PMBC's) is measured as follows. PBMC's are prepared from freshly taken blood or "buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested form TNFα by ELISA using commercially available kits.

In vivo activity in a skin eosinophilia model is determined by using the methods described by Hellewell et al, Br. J. Pharmacol. 111:811 (1994) and Br. J. Pharmacol. 110:416 (1993). Activity in a lung model is measured using the procedures described by Kallos and Kallos, Int. Archs. Allergy Appl. Immunol. 73:77 (1984), and Sanjar et al, Br. J. Pharmacol. 99:679 (1990).

An additional lung model, which allows measurement of inhibition of the early and late-phase asthmatic responses and also the inhibition of airway hyperreactivity, is described by Broadley et al, Pulmonary Pharmacol. 7:311 (1994), J. Immunological Methods 190:51 (1996) and British J. Pharmacol. 116:2351 (1995). Compounds of the invention show activity in this model.

Abbreviations
LPS Lipolysaccharide (endotoxin)
ELISA Enzyme linked immunosorbent assay

We claim:
1. A compound of the formula (i)

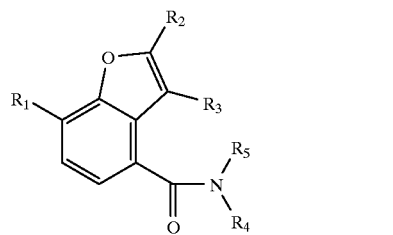

(i)

wherein
$R_1$ represent alkoxy optionally substituted with one or more halogens;
either $R_2$ and $R_3$, which may be the same or different, are each selected from the group consisting of H, CO-heteroaryl, CO-alkylaryl, alkyl-CO-alkyl, alkyl-CO-heteroaryl, and alkyl-CO-alkylaryl, provided that $R_2$ and $R_3$ are not both H; and $R_5$ is selected from the group consisting of aryl, heteroaryl, heterocyclo, arylalkyl, heteroarylalkyl, and heterocycloalkyl;
or $R_2$ and $R_3$ are the same or different and each are selected from the group consisting of H, aryl, arylalkyl, heteroaryl, alkyl, and CO-alkyl; and $R_5$ is selected from aryl and heteroaryl (except 4-pyridyl) optionally substituted with one or more substituents $R_{13}$ or alkyl-$R_{13}$;
$R_4$ is selected from the group consisting of H, arylalkyl, heteroarylalkyl, heterocycloalkyl, $S(O)_mR_{10}$ and alkyl optionally substituted with one or more substituents chosen from hydroxy, alkoxy, $CO_2R_7$, $SO_2NR_{11}R_{12}$, $CONR_{11}R_{12}$, —CN, carbonyl oxygen, $NR_8R_9$, $COR_{10}$ and $S(O)_nR_{10}$;
for $R_4$ and/or $R_5$, the aryl/heteroaryl/heterocycloportion may be optionally substituted with one or more substituents alkyl-$R_{13}$ or $R_{13}$;

$R_7$ is selected from the group consisting of H, alkyl, arylalkyl, heteroarylalkyl and heterocycloalkyl;
$R_8$ is selected from the group consisting of H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl;
$R_{10}$ is selected from the group consisting of alkyl, aryl, heteroaryl, heterocyclo, arylalkyl, heteroarylalkyl and heterocycloalkyl;
$R_9$, $R_{11}$ and $R_{12}$, which may be the same or different, are each selected from the group consisting of H and $R_{10}$;
$R_{13}$ is selected from the group consisting of alkyl optionally substituted by one or more halogens, alkoxy, aryl, heteroaryl, heterocyclo, hydroxy, aryloxy, heteroaryloxy, heterocyclooxy, arylalkyloxy, heteroarylalkyloxy, heterocycloalkyloxy, $CO_2R_7$, $CONR_{11}R_{12}$, $SO_2NR_{11}R_{12}$, halogen, —CN, —$NR_8R_9$, $COR_{10}$, $S(O)_nR_{10}$ and carbonyl oxygen;
m represents 1 or 2;
n represents 0–2;
or a pharmaceutically-acceptable salt thereof.

2. The compound, according to claim 1, wherein $R_5$ is selected from the group consisting of aryl and heteroaryl, which group is optionally substituted with one or more substituents $R_{13}$ and alkyl-$R_{13}$.

3. The compound, according to claim 2, wherein $R_4$ is selected from the group consisting of H and alkyl.

4. The compound, according to claim 3, wherein $R_2$ and $R_3$ are independently selected from the group consisting of H, CO-heteroaryl, CO-alkylaryl, alkyl-CO-alkyl, alkyl-CO-heteroalkyl and alkyl-CO-alkylaryl, provided that $R_2$ and $R_3$ are not both H.

5. The compound, according to claim 3, wherein $R_2$ and $R_3$ are independently selected from the group consisting of H, aryl, arylalkyl, heteroaryl, alkyl and CO-alkyl; and $R_5$ is not 4-pyridyl.

6. The compound, according to claim 1, wherein
$R_{13}$ is selected from the group consisting of aryl, heteroaryl, heterocyclo, hydroxy, alkoxy, aryloxy, heteroaryloxy, heterocyclooxy, arylalkoxy, heteroarylalkyloxy, heterocycloalkyloxy, $CO_2R_7$, $CONR_{11}R_{12}$, $SO_2NR_{11}R_{12}$, halogen, CN, $NR_8R_9$, $COR_{10}$, $S(O)_nR_{10}$ and carbonyl oxygen.

7. The compound, according to claim 1, wherein $R_2$ and $R_9$ are independently selected from the group consisting of H and alkyl.

8. The compound, according to claim 1, selected from the group consisting of
2-ethyl-7-methoxy-4-[N-(2-chloro-5-carboxy)phenyl] benzofuran carboxamide,
2-ethyl-7-methoxy-4-[N-(2,6-dichloro-4-carboxy)phenyl]-benzofuran carboxamide,
2-ethyl-7-methoxy-4-[N-(5-chloropyrimidin-4-yl)] benzofuran carboxamide,
2-ethyl-7-methoxy-4-[N-(3-methylthiotriazin-5-yl)] benzofuran carboxamide,
2-ethyl-7-methoxy-4-[N-(4-pyrido[3,2-b]pyridinyl)] benzofuran carboxamide, and
2-[(pyridin-4-yl)carbonyl]-7-methoxy-4-[N-(3,5-dichloropyridin-4-yl]benzofuran carboxamide.

9. The compound, according to claim 1, selected from the group consisting of
2-acetyl-7-methoxy-4-[N-(2-chlorophenyl)] benzofurancarboxamide, 2-acetyl-7-methoxy-4-[N-(2,6-dimethylphenyl)]
   benzofurancarboxamide,
2-acetyl-7-methoxy-4-[N-(4-methoxyphenyl)]
   benzofurancarboxamide,
2-acetyl-7-methoxy-4-[N-(3-bromo-5-methylpyrid-2-yl)]
   benzofurancarboxamide,
2-acetyl-7-methoxy-4-[N-(3-methylphenyl)]
   benzofurancarboxamide,
2-acetyl-7-methoxy-4-[N-(3,5-dichloropyrid-2-yl)]
   benzofurancarboxamide,
2-acetyl-7-methoxy-4-[N-(2-methylphenyl)]
   benzofurancarboxamide,
2-acetyl-7-methoxy-4-[N-(4-methoxy-2-methylphenyl)]
   benzofurancarboxamide,
2-acetyl-7-methoxy-4-[N-(pyrimidin-4-yl)]
   benzofurancarboxamide,
2-acetyl-7-methoxy-4-[N-(2-trifluoromethylphenyl)]
   benzofurancarboxamide,
2-acetyl-7-methoxy-4-[N-(2-ethylphenyl)]
   benzofurancarboxamide,
2-acetyl-7-methoxy-4-[N-(3-methylpyrid-2-yl)]
   benzofurancarboxamide,
2-ethyl-7-methoxy-4-[N-(2-chloropyrid-3-yl)]
   benzofurancarboxamide,
2-acetyl-7-methoxy-4-[N-(2-methoxyphenyl)]
   benzofurancarboxamide,
2-acetyl-7-methoxy-4-[N-(2-chloropyrid-3-yl)]
   benzofurancarboxamide,
2-acetyl-7-methoxy-4-[N-(2-chloro-6-methylphenyl)]
   benzofurancarboxamide,
2-ethyl-7-methoxy-4-[N-(3-carboxyphenyl)]
   benzofurancarboxamide, and
2-ethyl-7-methoxy-4-[N-(4-carboxyphenyl)]
   benzofurancarboxamide.

10. A compound of claim 1, selected from the group consisting of
7-methoxy-2-(2-thiazolocarbonyl)-4-[N-(5-chloropyrimidin-4-yl)]benzofurancarboxamide,
2-ethyl-7-methoxy-4-[N-(2,5-difluoropyrimidin-4-yl)]benzofurancarboxamide, and
2-ethyl-7-methoxybenzofuran-4-[(N-(1,3,5-trimethylpyrazol-4-yl)]carboxamide.

11. A compound selected from the group consisting of 2-acetyl-7-methoxy-4-[N-(3,5-dichloropyrid-4-yl)]benzofurancarboxamide and 2-acetyl-7-methoxy-4-[N-(pyrid-4)benzofurancarboxamide.

12. The compound, according to claim 1, in the form of an enantiomer of mixture of enantiomers.

13. A pharmaceutical composition for therapeutic use comprising a compound of claim 1 and a pharmaceutically-acceptable carrier or excipient.

14. A method for the treatment of a disease state capable of being modulated by inhibition of phosphodiesterase IV or Tumor Necrosis Factor, which comprises administering to a patient in need thereof an effective amount of a compound of claim 1.

15. The method, according to claim 14, wherein the disease state is a pathological condition associated with a function of phosphodiesterase IV, eosinophil accumulation or a function of the eosinophil.

16. The method, according to claim 15, wherein the pathological condition is selected from the group consisting of asthma, chronic bronchitis, chronic obstructive airways disease, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke and intermittent claudication.

17. The method, according to claim 15, wherein the pathological condition is selected from the group consisting of chronic bronchitis, allergic rhinitis and adult respiratory distress syndrome.

18. The method, according to claim 14, wherein the disease state is capable of being modulated by TNF inhibition.

19. The method, according to claim 18, wherein the disease state is an inflammatory disease or autoimmune disease.

20. The method, according to claim 19, wherein the disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption diseases, reperfursion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, ana-phylactoid purpura nephritis, chronic glomerulonephritis, inflammatory bowel disease and leukemia.

21. The method, according to claim 14, wherein the disease state is asthma.

22. The method, according to claim 20, wherein the disease state is acute respiratory distress syndrome, pulmonary inflammatory disease or pulmonary sarcoidosis.

23. The method, according to claim 20, wherein the disease state is joint inflammation.

24. The method, according to claim 14, wherein the disease state is a disease or disorder of the brain.

25. The method, according to claim 18, wherein the disease state is a yeast or fungal infection.

26. A method of gastroprotection, which comprises administering to a patient in need thereof an effective amount of a compound of claim 1.

27. A method of providing an analgesic, anti-tussive or anti-hyperalgesic effect in the treatment of neurogenic inflammatory disease associated with irritation and pain, which comprises administering to a patient in need thereof an effective amount of a compound of claim 1.

28. A method of treating asthma, which comprises co-administering to a patient in need thereof a compound of claim 1 and an anti-asthma drug selected from the group consisting of bronchodilators, steroids, and xanthines.

29. The method, according to claim 24, wherein said disease state is selected from the group consisting of brain trauma, stroke, ischaemia, Huntingdon's disease, and tardive dyskinesia.

* * * * *

UNITED STATES PATENT AND TRADEMARK OFFICE
CERTIFICATE OF CORRECTION

PATENT NO.    :    5,925,636

DATED         :    July 20, 1999

INVENTOR(S)   :    Hazel Joan Dyke, Christopher Lowe, John Gary Montana

It is certified that error appears in the above-identified patent and that said Letters Patent is hereby corrected as shown below:

Column 19, line 45: "represent" should read --represents--.

Column 21, line 46: "(pyrid-4)benzofurancarboxamide." should read --(pyrid-4-yl) benzofurancarboxamide.--.

Signed and Sealed this

Twenty-fifth Day of January, 2000

Attest:

Attesting Officer

*Acting Commissioner of Patents and Trademarks*